United States Patent [19]

Grasselli et al.

[11] 4,323,703

[45] Apr. 6, 1982

[54] PROCESS FOR THE OXIDATION OF OLEFINS TO ALDEHYDES AND ACIDS

[75] Inventors: Robert K. Grasselli, Garfield Heights; Arthur F. Miller, Cleveland; Harley F. Hardman, Lyndhurst, all of Ohio

[73] Assignee: Standard Oil Company, Cleveland, Ohio

[21] Appl. No.: 800,981

[22] Filed: May 26, 1977

Related U.S. Application Data

[63] Continuation of Ser. No. 676,039, Apr. 12, 1976, abandoned, which is a continuation of Ser. No. 112,782, Feb. 4, 1971, abandoned.

[51] Int. Cl.$^3$ .................... C07C 51/25; C07C 45/35
[52] U.S. Cl. .................... 562/546; 252/435; 252/437; 252/468; 260/465.3; 562/512.2; 568/469.9; 568/479; 568/480

[58] Field of Search .................. 260/533 N, 604 R; 252/435, 437, 468; 562/546, 512.2; 568/479, 480, 469.9

[56] References Cited

U.S. PATENT DOCUMENTS 3,642,930  2/1972  Grasselli et al. ............. 260/533 N

*Primary Examiner*—Vivian Garner
*Attorney, Agent, or Firm*—David J. Untener; Larry W. Evans; Herbert D. Knudsen

[57] ABSTRACT

The process comprises the vapor phase oxidation of lower molecular weight olefins to the corresponding unsaturated aldehydes and unsaturated carboxylic acids in the presence of a catalyst comprising the oxides of iron, bismuth, molybdenum and at least one element of the Group II elements as essential components, and optionally the oxides of phosphorus, arsenic and an alkali metal.

13 Claims, No Drawings

PROCESS FOR THE OXIDATION OF OLEFINS TO ALDEHYDES AND ACIDS

This is a continuation of application Ser. No. 676,039 filed Apr. 12, 1976, which was a continuation of application Ser. No. 112,782 filed Feb. 4, 1971, both now abandoned.

The present invention relates to a process for the catalytic oxidation of olefins to useful oxygenated hydrocarbon compounds. More particularly this invention relates to a process for the conversion of lower molecular weight alpha-olefins such as propylene and isobutylene to the corresponding unsaturated aldehydes and unsaturated carboxylic acids, acrolein, methacrolein, acrylic acid and methacrylic acid, respectively.

The process of this invention comprises contacting in the vapor phase a gaseous mixture of the olefin and oxygen with a solid catalyst containing the oxides of iron, bismuth, molybdenum and at least one element selected from Group II of the Periodic Classification of elements, as essential components, and optionally the oxides of phosphorus, arsenic, and an alkali metal.

The catalyst of this invention has a number of advantages that contribute greatly to the efficient and economic operation of the process. The catalyst has excellent redox stability under the reaction conditions of the process. Further the catalyst exhibits high activity and selectivity for the conversion of olefins to useful oxygenated products at a low bismuth content; therefor the cost of the essential components of the catalyst is low. This low cost of catalytic ingredients coupled with the ease of catalyst preparation make this catalyst very attractive from an economic standpoint.

The high activity of this catalyst at a low bismuth content is surprising in view of the conversions reported in U.S. Pat. No. 2,941,007 issued June 14, 1960 which describes a process for the production of unsaturated aldehydes and ketones from alpha-olefins in the presence of a catalyst consisting of bismuth molybdate or bismuth phosphomolybdate, and in view of the conversions reported in U.S. Pat. No. 3,171,859 which describes a process for producing unsaturated aldehydes in the presence of a catalyst comprising the oxides of iron, bismuth, phosphorus and molybdenum.

A further advantage associated with the process of this invention is the ability of this process to convert olefins directly to unsaturated aliphatic acids. Under the proper conditions, high yields of unsaturated aliphatic acids can be obtained directly by the oxidation of olefins, and the plant investment in a commercial single-step process for converting, for example, propylene to acrylic acid is considerably lower than for the two-step process.

The reactants employed in producing the unsaturated aldehydes and unsaturated carboxylic acids of this invention are oxygen and a lower alkene such as propylene or isobutylene, and mixtures thereof. The olefins may be in admixture with paraffinic hydrocarbons, such as ethane, propane, butane and pentane; for example, a propylene-propane mixture may constitute the feed. This makes it possible to use ordinary refinery streams without special preparation. Likewise, diluents such as nitrogen and the oxides of carbon may be present in the reaction mixture without deleterious effect.

In its preferred aspect, the process comprises contacting a mixture comprising propylene or isobutylene, and oxygen with the catalyst at an elevated temperature and at atmospheric or near atmospheric pressure.

Any source of oxygen may be employed in this process. For economic reasons, however, it is preferred that air be employed as the source of oxygen. From a purely technical viewpoint, relatively pure molecular oxygen will give equivalent results. The molar ratio of oxygen to the olefin in the feed to the reaction vessel should be in the range of 5:1 to 0.5:1 and a ratio of about 1:1 to 3:1 is preferred.

We have found that in some cases water in the mixture fed to the reaction vessel improves the selectivity of the reaction and the yield of unsaturated aldehydes and/or acids. However, water is not essential inasmuch as water is formed in the course of the reaction. In general, the molar ratio of added water to olefin, when water is added, is in the range of about 0.25 to 20:1. Ratios on the order of 1:1 to 4:1 are particularly desirable.

The reaction is carried out at a temperature within the range of from about 500° to about 900° F. The preferred temperature range is from about 550° to 750° F.

The pressure at which the reaction is conducted has some effect on conversion and the reaction should be carried out at about atmospheric or slightly above atmospheric (2 to 5 atmospheres) pressure.

The apparent contact time is not critical, and contact times in the range of from 0.1 to about 50 seconds may be employed. The optimum contact time will, of course, vary depending upon the olefin being reacted, but in general, a contact time of from 1 to 15 seconds is preferred.

The yield of unsaturated carboxylic acids is favored by higher reaction temperatures, higher ratios of oxygen to olefin and longer contact times, and the converse is true of the yields of unsaturated aldehydes. When maximum yield of unsaturated acids is desired, it is propitious to recycle the formed unsaturated aldehyde over the catalysts of the instant invention. The recycle of the unsaturated aldehyde can be combined with the recycle of process steam and/or unreacted olefin.

Generally any apparatus of the type suitable for carrying out oxidation reactions in the vapor phase may be employed in the execution of this process. The process may be conducted either continuously or intermittently. The catalyst bed may be a fixed-bed employing a large particulate or pelleted catalyst or, alternately a so-called "fluidized" bed of catalyst may be employed. The fluid reactor may comprise an open column or the reactor may contain a plurality of perforated trays stacked horizontally throughout the length of the column, as described in U.S. Pat. No. 3,230,246 issued Jan. 18, 1966.

The reactor may be brought to the reaction temperature before or after the introduction of the reaction feed mixture. However, in a large scale operation it is preferred to carry out the process in a continuous manner, and in such a system the circulation of the unreacted olefin is contemplated. Although the catalyst is redox stable, if necessary, regeneration or reactivation of the catalyst may be accomplished by contacting the catalyst with air at an elevated temperature.

The products of the reaction may be recovered by any of the methods known to those skilled in the art. One such method involves scrubbing the effluent gases from the reactor with cold water or an appropriate solvent to remove the products of the reaction. The ultimate recovery of the products may be accomplished by conventional means. The efficiency of the scrubbing operation may be improved when water is employed as the scrubbing agent by adding a suitable wetting agent in the water. Where molecular oxygen is employed as the oxidizing agent in this process, the resulting product mixture remaining after the removal of the carbonyl and carboxylic acid compounds may be treated to remove carbon dioxide and water with the remainder of the mixture containing the unreacted olefin and oxygen being recycled through the reactor. In the case where air is employed as the oxidizing agent in lieu of molecular oxygen the residual product after separation and other carbonyl products may be scrubbed with a nonpolar solvent, e.g., a hydrocarbon fraction in order to recover unreacted olefin, and in this case the remaining gases may be discarded. The addition of a suitable inhibitor to prevent polymerization of the unsaturated products during the recovery steps is also contemplated.

The catalyst useful in the process of the present invention is a mixture, complex or compound of the oxides of iron, bismuth, molybdenum, and at least one element from Group II of the Periodic Classification, and optionally the oxides of phosphorus and/or arsenic, and an alkali metal. The composition is conveniently expressed in the following empirical formula:

$$A_aB_bC_cFe_dBi_eMo_fO_x$$

wherein A is an alkali metal, B is phosphorus or arsenic or both, and C is at least one element selected from Group II A and Group II B of the Periodic Classification of elements, and wherein (a) is a number from 0 to less than 0.1, (b) is a number from 0 to 3, (c) is a number from 0.1 to 10, (d) and (e) are each a number from 0.1 to 6, (f) is a number from 8 to 16, and (x) is a number determined by the valence requirements of the other elements present. A preferred catalyst composition is one in which A is potassium, C is a Group II A metal, and the atom ratios of the elements in the foregoing empirical formula are within the range wherein (a) is a number from 0 to 0.09, (b) is from 0 to 1, (c) is a number from 0.1 to 7, (d) and (e) are each a number of from 1 to 4, and (f) is 12. Most preferred is a catalyst composition wherein the Group II A metal is magnesium.

The catalyst of this invention may be prepared by any of the numerous methods of catalyst preparation which are known to those skilled in the art. For example, the catalyst may be manufactured by co-precipitating the various ingredients. The co-precipitated mass may then be dried and ground to an appropriate size. Alternately, the co-precipitated material may be slurried and spray-dried in accordance with conventional techniques. The catalyst may be extruded as pellets or formed into spheres in oil as is well-known in the art. Alternatively, the catalyst components may be mixed with the support in the form of the slurry followed by drying, or they may be impregnated on silica or other supports.

A particularly attrition-resistant form of the catalyst may be prepared by adding the support material to the catalyst in two stages, first by preparing and heat-treating a mixture of active catalyst components and from 0 to 60 percent by weight of the total support material, followed by adding the remainder of the support material to the powdered form of the heat-treated catalyst. A more detailed description of the preparation of an attrition-resistant catalyst may be obtained from the examples.

The alkali metal may be introduced into the catalyst as an oxide or as any salt which upon calcination will yield the oxide. Preferred salts are the nitrates which are readily available and easily soluble.

Bismuth may be introduced into the catalyst as an oxide or as any salt which upon calcination will yield the oxide. Most preferred are the water-soluble salts which are easily dispersible within the catalyst and which form stable oxides upon heat-treating. The most preferred salt for introducing bismuth is bismuth nitrate.

To introduce the iron component into the catalyst one may use any compound of iron which, upon calcination, will result in the oxides. As with the other elements, water-soluble salts are preferred for the ease with which they may be uniformly dispersed within the catalyst. Most preferred is ferric nitrate. The Group II metals may be similarly introduced. However, the Group II metals may also be introduced into the catalyst as the insoluble carbonates or hydroxides which upon heat-treating result in the oxides.

To introduce the molybdenum component, any molybdenum oxide such as the dioxide, trioxide, pentoxide, or sesquioxide may be used; more preferred is a hydrolyzable or decomposable molybdenum salt such as a molybdenum halide. A preferred starting material is ammonium heptamolybdate.

Arsenic may be introduced as orthoarsenic acid. Phosphorus may be introduced as a salt of an alkali metal, an alkaline earth metal, or the ammonium salt, but is preferably introduced as phosphoric acid.

Other elements may be introduced, starting with the metal, oxidizing the metal with an oxidizing acid such as nitric acid, and then incorporating the nitrate into the catalyst. Generally, however, the nitrates are readily available and form a very convenient starting material.

Other variations in starting materials will suggest themselves to one skilled in the art, particularly when the preferred starting materials mentioned hereinabove are unsuited to the economics of large-scale manufacture. In general, any compounds containing the desired catalyst components may be used provided that they result in the oxides of the instant catalyst upon heating to a temperature within the range disclosed hereinafter.

The catalyst can be employed without a support and will display excellent activity. The catalyst can also be combined with a support, and preferably it is combined with at least 10 percent up to about 90 percent of the supporting compound by weight of the entire composition. Any known support materials can be used, such as, for example, silica, alumina, zirconia, titania, Alundum, silicon carbide, alumina-silica, the inorganic phosphates such as aluminum phosphate, silicates, aluminates, borates, carbonates, and materials such as pumice, montmorillonite, and the like, that are stable under the reaction conditions to be encountered in the use of the catalyst.

The catalytic activity of the system is enhanced by heating at an elevated temperature. Generally, the catalyst mixture is dried and heated at a temperature of from about 500° to about 1800° F., preferably at about 900° to 1300° F., for from about one to twenty-four hours or more. If activity then is not sufficient, the catalyst can be further heated at a temperature above about 1000° F. but below a temperature deleterious to the catalyst.

In general, activation of the catalyst is achieved in less time at the higher temperatures. The sufficiency of activation at any given set of conditions is ascertained by a spot test of a sample of the material for catalytic activity. Activation is best carried out in an open chamber, permitting circulation of air or oxygen, so that any oxygen consumed can be replaced.

Further, pre-treatment or activation of the catalyst before use with a reducing agent in the presence of a limited amount of air at a temperature in the range of 500° to 1000° F. is also beneficial.

A preferred method of preparing the catalyst of this invention and a more complete description of the process of the present invention can be obtained from the following examples.

In addition to the production of unsaturated aldehydes and carboxylic acids, the catalyst of this invention is also useful for the conversion of olefins such as propylene and isobutylene in admixture with ammonia to the corresponding unsaturated nitriles.

EXAMPLES 1–4

The catalysts in these examples were prepared according to the procedures described in U.S. Pat. Nos. 2,941,007 and 3,171,859, respectively.

EXAMPLES 5, 7–9, AND 11–14

The catalysts employed in the examples of this invention were prepared by essentially the same procedure as described herein below using the appropriate starting materials. A catalyst having the composition 80 wt.%-$K_{0.07}Mg_{4.5}Fe_4Bi_2P_{0.5}Mo_{12}O_{51}$-20 wt.%-$SiO_2$ was prepared by dissolving 70.6 grams of $(NH_4)_6Mo_7O_{24}.4H_2O$ in water with a minimum amount of heating. To this were added in succession with stirring, 1.9 grams of $H_3PO_4$ (85 wt.%) and 76.7 grams of DuPont Ludox AS (30 wt.%) colloidal silica sol. The solution was stirred for 15 minutes at room temperature. 53.7 Grams of $Fe(NO_3)_3.9H_2O$ dissolved in water were added to this solution followed by the successive addition of 38.5 grams of $Mg(NO_3)_2.6H_2O$, 0.23 grams $KNO_3$, and 32.4 grams of $Bi(NO_3)_3.5H_2O$ dissolved in water containing 8 cc of concentrated $HNO_3$ (68 wt.%). The slurry was heated with constant stirring until gel formation occurred. The gel was then dried at approximately 270° F. The resulting catalyst was heat-treated at 600° F. for 5 hours and at 1020° F. for 20 hours, and was then sized to 20–35 Tyler screen mesh.

EXAMPLE 6

An unsupported catalyst having the composition $Mg_{4.5}Fe_4Bi_2P_{0.5}Mo_{12}O_{51}$ was prepared by dissolving 70.6 grams of $(NH_4)Mo_7O_{24}.4H_2O$ in water with a minimum amount of heating, to which 1.9 grams of $H_3PO_4$ (85 wt.%) were added. The solution was stirred for 15 minutes at room temperature. 53.7 Grams of $Fe(NO_3)_3.9H_2O$ dissolved in water were added to this solution followed by the successive addition of 38.5 grams of $Mg(NO_3)_2.6H_2O$, and 32.4 grams of $Bi(NO_3)_3.5H_2O$ dissolved in water containing 6 cc of concentrated $HNO_3$ (68 wt.%). The slurry was heated with constant stirring until gel formation occurred. The gel was then dried at approximately 270° F. The resulting catalyst was heat-treated at 600° F. for 5 hours and at 1020° F. for 20 hours, and was then sized to 20–35 Tyler screen mesh.

EXAMPLE 10

An attrition-resistant catalyst having the composition 60 wt.%-$Mg_{4.5}Fe_4Bi_2P_{0.5}Mo_{12}O_{51}$-40 wt.% $SiO_2$ was prepared by dissolving 706 grams of $(NH_4)_6Mo_7O_{24}.4H_2O$ in 570 cc of water, using minimum heating, and then blending with 19 grams of 85% $H_3PO_4$. To this solution were added 767 grams of 30 percent silica sol (DuPont AS Ludox), followed by the successive addition of an aqueous solution containing 537 grams of $Fe(NO_3)_3.9H_2O$ in 250 cc water, and an aqueous solution containing 385 grams of $Mg(NO_3)_2.6H_2O$ in 190 cc water. To this vigorously stirred solution was added a solution composed of 324 grams of $Bi(NO_3)_3.5H_2O$, 30 cc of 68% $HNO_3$ and 380 cc of water. The slurry was heated with stirring until a non-fluid cake was obtained. The solid was then treated at a temperature of 600° F. for a period of 5 hours. After pulverizing the dry solid mechanically, 1000 grams of powder were blended with 1125 grams of 30% silica sol (DuPont AS Ludox) and sufficient water to result in a 40 wt.% solids slurry. The blend was ball-milled in a porcelain ball-mill for 20 hours. The resulting slurry was then spray-dried in a 4½ foot diameter Bowen spray-drier with an inlet temperature of 550° F., and an outlet temperature of 350° F. The microspheroidal product from the spray-drier was put into a furnace at 280° F. The temperature was raised to 600° F. over a period of one hour and maintained at that temperature for three hours. A final calcination of 15 hours duration at 1100° F. is imposed upon the catalyst prior to charging the material to the fluid bed reactor for testing.

EXAMPLE 16

A catalyst having the composition 80 wt.%-$K_{0.07}Mg_{4.5}Fe_4Bi_2P_{0.5}Mo_{12}O_{51}$ wt.%-$SiO_2$ was prepared as follows:

212 Grams of $(NH_4)_6Mo_7O_{24}.4H_2O$ were dissolved in water with a minimum amount of heating. 5.7 Grams of $H_3PO_4$ (85 wt.%) and 230 grams of DuPont Ludox AS (30 wt.%) colloidal silica sol were added in succession with stirring. 161 Grams of $Fe(NO_3)_3.9H_2O$ dissolved in water were added to this solution followed by the successive addition of 115.5 grams $Mg(NO_3)_2.6H_2O$ and 0.69 grams $KNO_3$ dissolved in water. To this vigorously stirred slurry are added 97.2 grams of $Bi(NO_3)_3.5H_2O$ dissolved in water containing 9 cc of concentrated $HNO_3$ (68 wt.%). The slurry was stirred constantly for about 15 minutes.

The slurry was then spray-dried and the powder obtained from the spray-drier was further dried in an oven at 230° F. for 16 hours. The resulting dry powder was well mixed with 1 wt.% graphite and compacted into 1/16"×3/16" pellets with a conventional pelleting machine. The pellets were heated for 5 hours at 450° F. to decompose the nitrates and were then calcined for 20 hours at 1020° F.

The reactor employed in carrying out the oxidation reactions in Examples 1 through 15 was a standard reactor with a fixed catalyst bed. The catalyst volume was about 5 cc and the catalyst mesh size was 20 to 35 Tyler screen mesh. The gases were metered to the reactor with rotameters. The products of the reaction were recovered by scrubbing the effluent gases from the reactor with water and were then analyzed by means of a gas chromatograph.

In the examples given, percent conversion to the unsaturated oxygenated hydrocarbon compounds was defined as follows: Mole percent per pass conversion to unsaturated aldehyde or to the unsaturated carboxylic acid =

$$\frac{\text{Mols of aldehyde or acid product obtained}}{\text{Mols of olefin fed}} \times 100$$

Oxidation reactions carried out with the catalyst compositions of this invention employing propylene and isobutylene as the hydrocarbon feeds are summarized in Tables I and II, respectively. These data are compared with conversions obtained with catalyst compositions of the prior art disclosed in U.S. Pat. Nos. 2,941,007 and 3,171,859 and shown in Examples 1 through 4 of Table I and in Example 14 of Table II. The data in these tables show that per pass conversions to acrolein, methacrolein, acrylic acid and methacrylic acid obtained with catalysts of the present invention are substantially higher than those obtained with catalysts of the prior art.

The catalysts of this invention gave comparable yields of unsaturated aldehydes and unsaturated acids in both the fixed bed and the fluid bed reactors employing, respectively, pelleted or fluid-type catalysts.

Group II A of the Periodic Classification of elements, and wherein (a) is a number greater than 0 to less than 0.1, (b) is a number from 0 to 3, (c) is a number from 0.1 to 10, (d) and (e) are each a number from 0.1 to 6, (f) is a number from 8 to 16, and (x) is a number determined by the valence requirements of the other elements present.

2. The process of claim 1 wherein said molecular oxygen-containing gas is air.

3. The process of claim 2 wherein the olefin is isobutylene.

4. The process of claim 2 wherein the olefin is propylene.

5. The process of claim 4 wherein the molar ratios of olefin to oxygen are within the range of 1:0.5 to 1:5.

6. The process of claim 5 carried out in the presence of steam.

TABLE I

CONVERSION OF PROPYLENE TO ACROLEIN AND ACRYLIC ACID
Feed Ratio (Molar): $C_3^=/Air/H_2O = 1/11/4$ Cat. Vol. - 5 cc  Pre-Run - 15 min.
Cat. Part. Size - 20-35 Mesh  Run Time - 30 min.

| Example | Catalyst Composition | React. Temp. (°F.) | Cont. Time (Sec) | Per Pass % Conversion to: Acrolein | Acrylic Acid |
|---|---|---|---|---|---|
| | | | | Molar Basis | |
| 1. | 50%-$Bi_9PMo_{12}O_{52}$-50% $SiO_2$ | 680 | 2.5 | 22.8 | 2.9 |
| 2. | " | 680 | 5.0 | 35.6 | 3.5 |
| 3. | 50%-$Fe_{4.5}Bi_{4.5}PMo_{12}O_{52}$-50% $SiO_2$ | 605 | 2.5 | 22.0 | 3.9 |
| 4. | " | 680 | 5.0 | 48.5 | 6.8 |
| 5. | 80%-$Mg_{6.5}Fe_3Bi_1P_{0.5}Mo_{12}O_{49}$-20% $SiO_2$ | 680 | 5.0 | 64.4 | 10.6 |
| 6. | 100%-$Mg_{4.5}Fe_4Bi_2P_{0.5}Mo_{12}O_{51}$ | 680 | 5.0 | 78.3 | 5.7 |
| 7. | 80%-$Mg_{4.5}Fe_4Bi_2P_{0.5}Mo_{12}O_{51}$-20% $SiO_2$ | 605 | 2.5 | 67.3 | 7.8 |
| 8. | " | 680 | 2.5 | 54.3 | 17.2 |
| 9. | 80%-$Mg_{4.5}Fe_4Bi_2P_{0.5}Mo_{12}O_{51}$-20% $SiO_2$ | 680 | 5.0 | 51.2 | 20.6 |
| 10. | 60%-$Mg_{4.5}Fe_4Bi_2P_{0.5}Mo_{12}O_{51}$-40% $SiO_2$ Attrit. Resistant (part. size 50-80 Mesh) | 605 | 2.5 | 64.2 | 8.6 |
| 11. | 80%-$K_{0.07}Mg_{4.5}Fe_4Bi_2P_{0.5}Mo_{12}O_{51}$-20% $SiO_2$ | 680 | 5.0 | 71.7 | 12.1 |
| 12. | 80%-$Mg_{4.5}Fe_4Bi_2As_{0.5}Mo_{12}O_{51}$-20% $SiO_2$ | 680 | 2.5 | 68.3 | 10.2 |
| 13. | 80%-$Mg_{4.5}Fe_4Bi_2Mo_{12}O_{50}$-20% $SiO_2$ | 680 | 2.5 | 65.9 | 5.3 |

TABLE II

CONVERSION OF ISOBUTYLENE TO METHACROLEIN AND METHACRYLIC ACID

Reaction Temp: 680° F.
Contact Time: 2.5 seconds
Molar ratio $IC_4^=/Air/H_2O = 1/11/4$

| Example | Catalyst Composition | Percent Per Pass Conversion to: Methacrolein | Methacrylic acid |
|---|---|---|---|
| | | Molar Basis | |
| 14. | 50%-$Fe_{4.5}Bi_{4.5}P_1Mo_{12}O_{52}$-50% $SiO_2$ | 28.6 | 4.0 |
| 15. | 100%-$Mg_{4.5}Fe_4Bi_2P_{0.5}Mo_{12}O_{51}$ | 48.5 | 4.8 |

We claim:

1. The process for the conversion of an olefin selected from the group consisting of propylene, isobutylene and mixtures thereof, to the corresponding unsaturated aldehydes and unsaturated carboxylic acids, comprising reacting in the vapor phase at a temperature of from about 500° to 900° F. and at a pressure of from about 0.5 to 5 atmospheres said olefin with a molecular oxygen-containing gas in the presence of a catalyst of the empirical formula:

$$A_aB_bC_cFe_dBi_eMo_fO_x$$

wherein A is an alkali metal, B is phosphorus or arsenic or both, and C is at least one element selected from 7. The process of claim 1 wherein said catalyst is supported on a support material.

8. The process in claim 7 wherein said catalyst is supported on a support material in amounts of from about 10 percent to about 95 percent by weight of the supported catalyst.

9. The process of claim 8 wherein the catalyst is prepared by the steps of:
(a) activating a mixture of said catalyst and from 0 to 60 percent by weight of the total support material at a temperature of from about 1000° F. to about 2000° F. in an oxidizing atmosphere, and reducing the resulting catalyst to a fine powder and
(b) mixing the powder from (a) with an aqueous slurry of the remaining support material, drying and heat-treating the resulting mixture at a temperature of from about 750° F. to about 2000° F.

10. The process in claim 1 wherein the Group II A element of said catalyst is magnesium.

11. The process of claim 1 carried out in the presence of a pelleted catalyst in a fixed bed reactor, and optionally in the presence of steam.

12. The process of claim 1 carried out in the presence of a fluidized catalyst, in a fluid bed reactor, and optionally in the presence of steam.

13. The process of claim 1 wherein the oxygen-containing gas is molecular oxygen, and the process is carried out in the presence of process steam.

* * * * *